United States Patent [19]

Stenn

[11] 4,431,582

[45] Feb. 14, 1984

[54] PROTEIN, COMPOSITION AND METHOD FOR ENHANCING EPITHELIAL CELL MOVEMENT

[75] Inventor: Kurt S. Stenn, Guilford, Conn.

[73] Assignee: Research Corporation, New York, N.Y.

[21] Appl. No.: 450,789

[22] Filed: Dec. 17, 1982

Related U.S. Application Data

[63] 1981, abandoned, which is a continuation of S.N. 244,963, Mar. 18, 1981 now abandoned, which is a continuation of S.N. 135,631, Mar. 31, 1980, now abandoned.

[51] Int. Cl.³ .............................................. C07G 7/00
[52] U.S. Cl. .......................... 260/112 B; 260/112 R; 424/101; 424/177
[58] Field of Search ........................ 260/112 B, 112 R; 424/101, 177

[56] References Cited

U.S. PATENT DOCUMENTS 3,122,476  2/1964  Gaeta ............................... 260/112 B
3,948,875  4/1976  Cohen et al. .................... 260/112 R
3,973,001  8/1976  Jaeger et al. .................... 260/112 B

OTHER PUBLICATIONS

British J. of Dermatology, vol. 98, pp. 411–416 (1978), Stenn.
Arch-Dermatol. Res. vol. 264, pp. 3–15 (1979), Stenn et al.
Brit. J. of Dermatology (1978), 99 pp. 513–518, Mitrani et al.
Biochem-Journal, vol. 185, No. 2, Feb. 1980, Whateley et al.

Primary Examiner—Howard E. Schain
Attorney, Agent, or Firm—Scully, Scott, Murphy & Presser

[57] ABSTRACT

A protein has been isolated from mammalian plasma or serum which enhances epithelial cell movement. A second factor which has no epithelial cell movement activity has also been isolated from mammalian plasma or serum which, when combined with the first protein, enhances the epithelial cell movement activity thereof.

5 Claims, 3 Drawing Figures

PROTEIN, COMPOSITION AND METHOD FOR ENHANCING EPITHELIAL CELL MOVEMENT

RELATED U.S. APPLICATION DATA

This application is a continuation-in-part of application Ser. No. 330,396, filed Dec. 14, 1981, now abandoned which is a continuation of application Ser. No. 244,963, filed Mar. 18, 1981, now abandoned which is a continuation of application Ser. No. 135,631, filed Mar. 31, 1980, now abandoned.

BACKGROUND OF THE INVENTION

It has long been suspected, and earlier studies have confirmed, that there is a specific factor or activity in mammalian serum and plasma which supports epidermal cell movement. [Stenn, *British Journal of Dermatology*, Vol. 98, pages 411 (1978); Stenn et al., *Arch. Dermatol. Res.*, Vol. 264, pages 3–15 (1979); U.S. Pat. No. 3,948,875].

Recently efforts have been directed toward the characterization of the epidermal cell migration promotion activity in serum. See Levene, M., *Br. J. Dermatol.*, Volume 86, pages 481–490 (1972); Coombs, V. A., Nissen, B. K. and Marks, R., *Arch. Dermatol. Forsch*, Vol. 249, pages 367–372 (1974); Stenn, K. S. and Dvoretzky, I., *Arch. Dermatol. Res.*, Vol. 264, pages 3–15 (1979); Mitrani, E. and Marks, R., *Br. J. Dermatol.*, Vol. 99, pages 513–518 (1978); Griffiths, G., Jones, H. M., Cryer, J., Kay, J. and Marks, R., *J. Invest. Dermatol.*, Vol. 46, 430 (abstr.) (19781); and Ooka, H., Yamauto, K., Okuma, Y., Suga, S. and Wakasugi, M., *Exp. Gerontol.*, Vol. 10, pages 79–83 (1975). Mitrani et al., for example, describe a method for fractionating serum by combining ammonium sulfate precipitation and molecular sieve chromatography.

Other spreading factors have been described [Lipton, A., Klinger, II, Paul, D. and Holley, R., *Proc. Natl. Acad. Sci. U.S.A.*, Vol. 68, pages 2799–2801 (1971); Wolf, L. and Lipton, A., *Exp. Cell. Res.*, Vol. 80, pages 499–502 (1973); Burk, R. R., *Proc. Natl. Acad. Sci. U.S.A.*, Vol. 70, pages 369–372 (1973); R. R. Burk, *Exp. Cell. Res.*, Vol. 101, pages 293–298 (1976); Wall, R. T., Harker, L. A. and Striker, G. E., *Lab Invest.*, Vol. 39, pages 523–529 (1978); Zetter, B. R., *Nature* (London), Vol. 285, pages 41–43 (1980); and Leonard, E. T. and Skeel, A., *Exp. Cell. Res.*, Vol. 102, pages 434–438 (1976)].

Recently a serum spreading factor for fibroblasts was isolated by Knox et al. (*Exp. Cell. Res.*, Vol. 123, pages 421–424 (1979)) and Whateley et al. (*Biochem. J.* Vol. 185, pages 349–354 (1980)) from fetal calf serum. The protein differs from the protein of the present invention by origin, purification and chemical properties and activity.

It is an object of the present invention to provide an epithelial cell movement enhancing protein and a method for its preparation.

SUMMARY OF THE INVENTION

The present invention provides a novel protein which enhances epithelial cell movement, in vitro and in vivo. The protein may be derived from human serum or plasma.

The protein is a single-chained, glycosylated, trypsin digestible, $\alpha_2$ serum globulin of apparent molecular weight 62,000 daltons, and an N-terminal amino acid sequence of ASN-SER-PRO-LEU-ASP-GLU. It is resistant to the protease inhibitors, diisopropyl fluorophosphate and phenyl methyl sulfonyl fluoride. It has an isoelectric point of 5.1–5.2, and an extinction coefficient of about 1. Antibody to the purified protein blocks all the epidermal cell spreading activity of human plasma (or serum); in addition, immunoelectrophoresis of the antisera against whole plasma (serum) reveals a single protein arc.

The protein may be prepared from human plasma or serum by ammonium sulfate fractionation from human serum or plasma and purified by ion-exchange and gel filtration chromatography, isoelectric precipitation and preparative polyacrylamide gel electrophoresis.

The present invention also provides an additional protein derived from human plasma or serum which does not itself enhance epithelial cell movement but does synergistically enhance more than 10-fold the epithelial cell movement activity of the above-described protein. The epithelial cell movement enhancing protein of the present invention will be referred to hereinafter as the "protein". The protein which enhances the epithelial cell movement activity of the "protein" will be referred to hereinafter as the "co-factor."

DETAILED DESCRIPTION OF THE INVENTION

Figure 1:
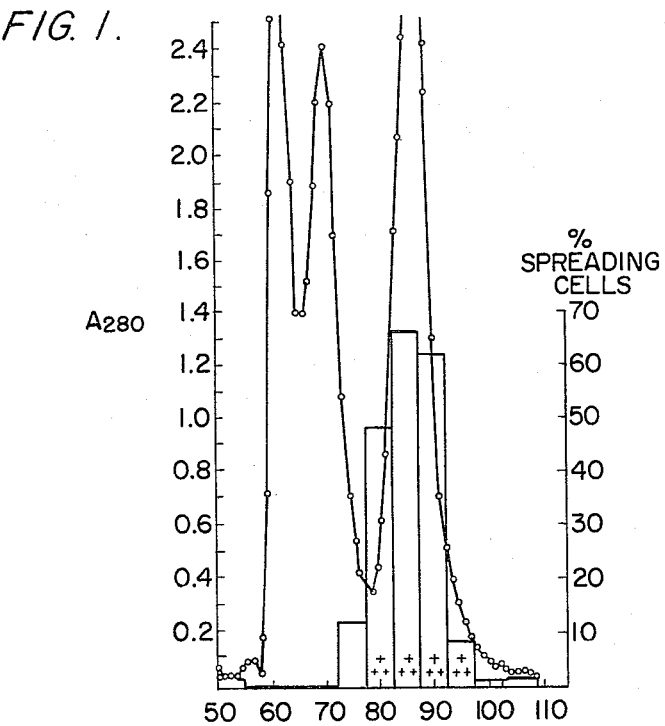

The protein of the present invention supports: (a) dissociated guinea pig epidermal cell spreading in vitro; (b) mouse ear skin epidermal sheet spreading in vitro; and (c) swordtail fish epidermal sheet spreading in vitro.

The purified protein will support cell spreading at a concentration of 10–20 μgm/ml if no other protein is present. If bovine serum albumin is present at 0.5 mg/ml, it will support spreading at 1 μgm/ml.

That the active factor is a protein is further substantiated by the following facts: (a) its spreading activity co-migrates on electrophoresis with Coomassie Blue-protein staining band; (b) its activity is destroyed by trypsin; (c) its amino acid composition is typical of proteins; (d) its activity corresponds to a molecule with the amino terminal sequence of $NH_2$-ASN-SER-PRO-LEU-ASP-GLU.

The protein is glycosylated as demonstrated by its periodic acid-Schiff staining on sodium dodecyl polyacrylamide gel electrophoresis and its binding to sugar-affinity lectin (Concanavalin B) resin. The protein is a single chain protein having an apparent molecular weight of approximately 62,000 daltons.

The protein also has the following electrophoretic properties; (a) it has an isoelectric point between 5.1–5.2; (b) compared to other human serum proteins it travels on immunoelectrophoresis with the $\alpha_2$ globulins.

The protein has the following amino acid content:

| Amino Acid | Residues per 1000 amino acids | Residues per 62,752 daltons |
|---|---|---|
| CYS | 4 | 2 |
| ASP | 111 | 62 |
| THR | 72 | 62 |
| SER | 81 | 46 |
| GLU | 119 | 67 |
| PRO | 35 | 19 |
| GLY | 46 | 26 |
| ALA | 77 | 43 |
| VAL | 59 | 33 |
| MET | 26 | 15 |
| ILE | 44 | 24 |
| LEU | 123 | 69 |

-continued

| Amino Acid | Residues per 1000 amino acids | Residues per 62,752 daltons |
|---|---|---|
| TYR | 22 | 12 |
| PHE | 56 | 31 |
| HIS | 21 | 12 |
| LYS | 60 | 34 |
| ARG | 37 | 21 |
| TRP | 7 | 4 |

Standard procedures for automated amino acid analysis with a DURRUM D-500 amino acid analyzer were used to determine the amino acid composition. The protein was hydrolyzed in 6 N HCL under vacuum for 20, 48, 72 and 110 hours. Cysteine residues were determined by performing acid oxidation according to the method of Moore (*J. Biol. Chem.* Vol. 238, pages 235 (1962)). Tryptophan residues were determined by mercaptoethanesulfonic acid hydrolysis according to the procedure of Penke, B., Fesencz, R., and Kovacs, K. (*Anal. Biochem.*, Vol. 60, page 45 (1974)).

The amino acid sequence of the N-terminal of the protein was determined automatically using the Beckman 890C sequence with a Sequemat P-6 autoconverter. Derivative analysis was conducted using a Water Associates HPLC with an automatic injector and programmed gradient elution. Norleucine was used as the internal standard, with the following results:

| Cycle Number | Predominant Amino Acid | Concentration |
|---|---|---|
| 1 | Asparagine | 1.57 $\mu$moles |
| 2 | Serine | 0.37 $\mu$moles |
| 3 | Proline | 1.81 $\mu$moles |
| 4 | Leucine | 2.62 $\mu$moles |
| 5 | Aspartic | 1.27 $\mu$moles |
| 6 | GLutamic | 1.73 $\mu$moles |

The determined amino terminal amino acid sequence is then $NH_2$-ASN-SER-PRO-LEU-ASP-GLU.

The extinction coefficient of the purified 75 kd protein was measured experimentally as about 1.0 using the Lowry assay (*J. Biol. Chem.*, Vol. 193, page 265 (1951) with bovine serum albumin as the standard. The determination indicates that 1 mg/mg solution of the purified protein has an absorbance of about 1.0 when using an ultraviolet wave length of 280 nm. The protein is prepared by:

(1) diluting mammalian plasma or serum with water, adjusting the pH thereof and dissolving therein sufficient ammonium sulfate to produce an approximately 33.3% saturated solution and removing the thus formed precipitates;

(2) dissolving in the supernatant sufficient ammonium sulfate to produce an approximately 66.7% saturated solution;

(3) removing the resultant precipitate from said solution, suspending it in water and dyalyzing the suspension against a buffered solution having a pH of about 6.0;

(4) placing the dialyzed fraction in a buffer solution and subjecting the solution to anionic chromatographic separation;

(5) eluting the chromatographically adherent fraction with an aqueous buffered solution having a pH of about 6.0 and an ionic strength of about 12 mmhos;

(6) dialyzing the eluted fraction against an aqueous buffer solution having a pH of about 6.0;

(7) subjecting the dialysand to isoelectric precipitation; and (8) subjecting the separated fraction to electrophoresis.

The "protein" enhances epithelial cell movement, in vivo and in vitro, and is useful in such applications as wound-healing, etc.

The "co-factor" increases the epithelial cell movement enhancement activity of the "protein" more than 10-fold, when combined with the "protein."

The invention is further illustrated by the following non-limiting examples wherein: All buffers were made 0.02% in $NaN_3$ and 0.1 mM in phenylmethylsulfonyl fluoride. Dialysis bags were prepared as described [Stenn, K. S. and Blout, E. R., *Biochemistry*, Vol. 11, page 4502 (1972)]. In all tissue culture experiments Dulbecco's modified Eagle's medium (DME medium) (GIBCO) containing antibiotics was used. The cultures were incubated at 35°–38° C. in 95° air/5% $CO_2$, in a water vapor-saturated environment. In a typical experiment the fractions to be tested were dialyzed against 0.1 mM Tris.HCl(pH 8.0) plus 100 mM NaCl then added to an appropriate volume of 2×DME medium and sterilized by Millipore filtration (0.45 $\mu$m pore diameter).

EXAMPLE 1

Preparation of Protein From Human Plasma

Human Plasma from normal donors 1–2 weeks after bleeding was cleared by centrifuging at 5000×g for 20 min. at 4° C. At 4° C., saturated solution of $(NH_4)_2SO_4$ was added to 1 liter of plasma. The precipitate occurring at 33.3% saturation was discarded after centrifugation (5000×g, 20 min., 4° C.). The 66.7% $(NH_2)_2SO_4$ precipitate was retained, solubilized in 400 ml of distilled water, and dialyzed against four changes of 4 liters of 50 mM $Na_2HPO_4/NaH_2PO_4$ (pH 6.0) for 24 hrs. The dialysand was added to a DEAE Bio-Gel A (100–200 mesh; Bio-Rad) column (8×8×23 cm) equilibrated with the dialysis buffer and the column was washed until the effluent had an absorbance at 280 nm of less than 0.05. The product of this washing step is the above noted "cofactor." The active fraction was eluted stepwise with 50 mM $NaH_2PO_4/Na_2HPO_4$ (pH 6.0) plus 100 mM NaCl, pooled, and dialyzed against three changes of 4 liters of 0.5 mM $NaH_2PO_4/Na_2HPO_4$ (pH 6.0) for 24 hrs. The dialysand was cleared by centrifugation and titrated to pH 5.3 with 0.1 mHCl with slow stirring. The supernatant was cleared by centrifugation and again titrated to pH 4.6. The precipitate was collected by centrifugation and then dissolved in 24 ml of 50 mM $NaH_2PO_4/Na_2HPO_4$ (pH 6.0) plus 100 nM NaCl. This isoelectric precipitation step was then repeated identically. The isolation precipitate solution was loaded onto a gel filtration column (Sephacryl S 200, Pharmacia 5×90 cm, equilibrated with 50 mM $NaH_2PO_4/Na_2HPO_4$ pH 6.0 plus 100 mM NaCl). The active fraction from gel filtration (approximately 4 mg protein) was applied to a polyacrylamide large slab gel (0.5×12×16 cm) (Davis, *Ann. N.Y. Acad. Sci.* Vol. 121, page 404 (1964)) across which a potential of 110 V was established. The active fraction ran with an $R_f$ value of 0.5–0.57. The active fraction was cut out and run on a second identical gel but following the conditions of Laemmli [*Nature*, Vol. 227, pages 680–685 (1970) 15% acrylamide]. The protein travelled as the only diffuse band on this gel. The protein was eluted from this gel electrophoretically at 100 volts using an apparatus described by Doly and Petek [*J. Chromatography*, Vol. 137, pages 69–81 (1977)]. The protein yield of this elution step was 2%. The eluate was washed with 50 mM NaH$_2$PO$_4$/Na$_2$HPO$_4$ (pH 6.0) plus 100 mM NaCl, concentrated (Amicon filter PM-30), and stored at room temperature.

EXAMPLE 2

Electrophoresis and Amino Terminal Analysis

Using the method of Laemmli (*Nature*, Vol. 227, page 680 (1970)) on sodium dodecyl sulfate polyacrylamide gel electrophoresis (SDS-PAGE) of 12.5% acrylamide the purified preparation shows a single, but somewhat diffuse, Coomassie-Blue staining band. After reduction with mercaptoethanol the mobility does not change. Compared to the electrophoretic mobility of standard proteins (phosphorylase b, 94 kd; bovine serum albumin 67 kd, ovalbumin 43 kd, carbonic anhydrase 30 kd, soybean trypsin inhibitor 20.1 kd; lactalbumin 14.4 kd) the cell spreading protein has a molecular weight of about 62 kd.

Amino-terminal amino acids analysis of the protein conducted by Edman degradation using an automated amino acid sequenator revealed one N-terminal amino acid, asparagine.

Exposing the purified fraction to a 0.5% trypsin solution for 15 min. at 37° C. led to complete destruction of spreading activity, thereby supporting the conclusion that the activity is a protein.

The yield of Example 1 is given in Table 1. Virtually all the spreading activity was present in the 66.7% (NH$_4$)$_2$SO$_4$ precipitate. In step 3 the dialyzed active ammonium sulfate fraction was placed on an anion-exchange resin (DEAE-Bio-Gel), washed copiously, and step eluted with 0.1 M NaCl. This fraction, when assayed alone, had no greater specific activity than the material placed on the column, even though considerable inactive protein had been removed. This observation suggested that a second component had been removed in the wash. Indeed, as shown in Table 1, adding the wash which contains the "co-factor" from the ion-exchange step (at a protein concentration of 0.5 mg/ml) to the assay enhanced specific activity more than 10-fold. The action fraction, purified further by isoelectric precipitation at pH 4.6, was poured over a gel filtration column and the active fractions were pooled. Finally, this concentrated preparation was separated in a preparative electrophoresis step. In this system the spreading activity travelled with an R$_f$ value of about 0.50–0.57.

TABLE 1

| | Specific Activity | | |
|---|---|---|---|
| Step | Assayed alone | Assayed with cofactor | Yield* % |
| 1. Human plasma | 195 | 220 | 100 |
| 2. 66.7% saturated (NH$_4$)$_2$SO$_4$ precipitate | 946 | 1,357 | 112 |
| 3. Ion-exchange chromatography fraction | 684 | 11,765 | 73 |
| 4. Isoelectric precipatate (pH 4.6) | 1167 | 16,250 | 32 |
| 5. Gel-filtration fraction | 1510 | 37,302 | 10 |
| 6. Preparative electrophoresis fraction | — | 60,000 | 2 |

The dissociated epidermal cell spreading assay was used.
*Yield assaus were determined in the presence of cofactor.

EXAMPLE 3

Assays

Three different epidermal cell spreading assays were employed: dissociated epidermal cell, explant outgrowth, and epiboly. For the dissociated epidermal cell assay 0.4-mm-thick sheets of truncal skin were removed from deeply anesthetized (ether) 200–250-g Hartley male guinea pig by using a dermatome after clipping the fur and treating with a depilatory cream. Epidermis (without dermal contamination, as judged by light microscopy) was stripped from this preparation after incubation at 37° C. for 30 min. to trypsin (GIBCO no. 7010) at 0.5 mg/ml in calcium and magnesium-free Tyrode's solution. Epidermal cells were shaken and scraped from the epidermis, centrifuged, suspended in DME medium, and counted (hemocytometer). Approximately 2×10$^5$ cells suspended in DME medium were placed in each Petri dish (34×10 mm, Falcon), and incubated at 37° C. After 2 hr the supernatant medium was discarded and replaced by test medium. At this time 10% of the cells were adherent but none were spread. After incubating 4–20 hrs in the test medium the number of spread cells per 100 attached nonkeratinized cells counted was determined by staining the cells with Giemsa stain, Stenn et al., supra. The number of spread cells divided by the protein concentration (mg) of the spreading fraction in the growth medium was expressed as spreading units. A cell was considered spread if its cytoplasm was distributed on the substratum in a radial or polar pattern, Vasiliev, J. M. and Gelfand, I. M., *Int. Rev. Cytol.* Vol. 50, pages 159–274 (1977). For the epidermal outgrowth assay and the epiboly studies the procedures of Stenn and Dvoretzky, supra, were followed.

Briefly, for the epidermal cell spreading assay mouse ear skin disks were laid onto plastic tissue culture Petri dishes and held down by a fibrin clot. The explants were gently overlaid with culture medium (DME plus the test fraction) and incubated for 3 days. At this time the maximal radial epidermal outgrowth from the explant edge was measured. For the epiboly experiments mouse ear skin explants were floated upon tissue culture medium (DME plus the test fraction) for 2 days and then Bouins, fixed, embedded, sectioned and stained histologically as previously described by Stenn et al., supra. The extent of epidermal movement about the lower surface of the explant was measured and expressed as a percent of lower surface covered by epithelium.

That spreading activity is not a property of all fractions in plasma is apparent from FIG. 1 which depicts the results of a gel filtration experiment. Virtually all spreading activity (with all three assays) was associated with a retained, smaller molecular weight, fraction. FIG. 1 represents an elution profile of human plasma by gel filtration and the identification of spreading activity. Five milliliters of whole human plasma was filtered through a 5×90 cm Bio-Gel P-200 column in a buffer of 0.01 M NaH$_2$PO$_4$/Na$_2$HPO$_4$ (pH 8.0)+0.1 M NaCl. Five-milliliter fractions were collected at a rate of 12 ml/hr. Each 10 tubes were pooled and tested by each of the three spreading assays dissociated cell assay (open bars) nonquantitated explant spreading (+), and epiboly (++),O———O, A$_{280}$. The abscissa represents fraction number minus 160.

Figure 2:
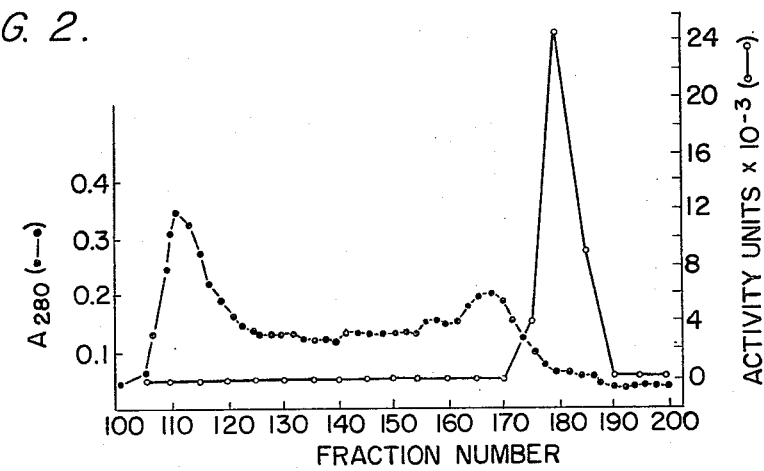

FIG. 2 depicts the gel filtration assay data of the active isoelectric precipitate. The gel (Sephacryl S-200, Pharmacia) was packed into a 5×90 cm column and equilibrated with 50 mM NaH$_2$PO$_4$/Na$_2$HPO$_4$ (pH 6.0)+100 mM NaCl. The 3-ml sample contained 50-60 mg of protein. The column was developed at the rate of 36 ml/hr and 3-ml fractions were collected. Protein elution was measured by absorbance at 280 nm (●) and spreading activity by the guinea pig dissociated epidermal cell assay (○).

Figure 3:
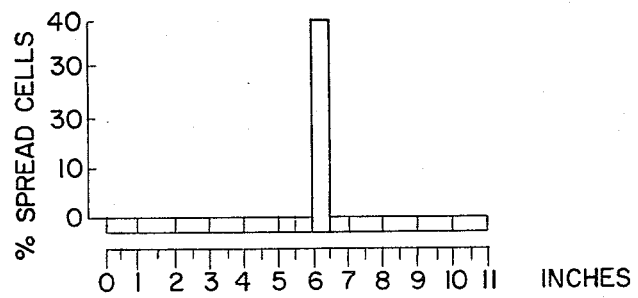

FIG. 3 depicts the polyacrylamide gel electrophoretic pattern of the ultimately purified protein and comigrating spreading activity. The Davis gel of the final step material is shown along the abscissa with the corresponding spreading activity recorded on the ordinate.

On SDS-PAGE electrophoresis the purified protein stains positive with the periodic acid-Schiff procedure following the method of Fairbanks et al. (*Biochemistry*, Vol. 10, page 2606 (1971) indicating that the protein is glycosylated. Additional evidence that the protein is glycosylated is that the epidermal spreading activity of serum is completely adsorbed by a sugar-binding lectin column (Concanavalin B-Sepharose Pharmacia, 50 mM NaH$_2$PO$_4$/Na$_2$HPO$_4$ (pH 6.0) and 100 mM NaCl).

EXAMPLE 4

Antibody Preparation and Properties

Antibody to the protein was produced in rabbits by injecting subcutaneously the purest preparation suspended in Freund's adjuvant. Protein (500 μgm/animal) was injected every 2 weeks over a 6 weeks period. Two weeks after the final injection blood was collected and serum prepared by allowing the blood to clot. The serum was made 40% saturated in ammonium sulfate and centrifuged. This immunoglobulin-rich precipitate fraction was dialyzed against phosphate buffered saline.

This antiserum was analyzed by immunoelectrophoresis using standard procedures. Briefly a 1% agarose gel in sodium barbital buffer pH 8.6 was layered over a glass slide. On each side of the slide a 2 mm diameter well was made and proteins were added. The preparation was placed across an electric potential for 1 hour at 4° C. Afterwards a long trough was made between the wells into which antiserum was added. This preparation was allowed to diffuse overnight at 24° C.

By immunoelectrophoresis the antiserum gave a single arc when run against the purified protein or whole human plasma or human serum. The antiserum was mixed with antihuman albumin and the immunoelectrophoresis repeated. The antiserum was also run with anti $\alpha_1$ antitrypsin or anti $\alpha_2$ macroglobulin.

By immunoelectrophoresis, the protein was shown to travel slower than albumin and $\alpha_1$ anti trypsin and slightly faster than $\alpha_2$ macroglobulin. By this technique its electrophoretic mobility was determined to be in the $\alpha_2$ globulin region of human serum protein.

Using the techniques of immunodiffusion and immunoelectrophoresis with purified protein, antibody, and serum proteins and their antibodies, no cross-reactivity (i.e., immunological identity) was found with human albumin, fibronectin, laminin, $\alpha_2$ macroglobulin, $\alpha_1$ antitrypsin, $\beta_2$ microglobulin, and collagens (Type I, III, IV, V).

Adding the immunoglobulin fraction of the antiserum to whole human plasma blocked the epidermal spreading activity of plasma. The immunoglobulin fraction of the antiserum was isolated by ammonia sulfate precipitation at 30% saturation. This fraction was then diluted and added to the culture media with various concentrations of human plasma (HP). The spreading of dissociated guinea pig epidermal cells was measured (Table 2):

TABLE 2

| Medium | Dissociated Epidermal Cell Spreading (% ± 1 S.D.) | |
|---|---|---|
| Medium 199 alone | 0 ± 0 | 0 ± 0 |
| Medium 199 ± antisera (1:10) | 0 ± 0 | 0 ± 0 |
| Medium 199 + HP (1:500) | 46 ± 7 | 46 ± 7 |
| Medium 199 + HP (1:500) + antisera (1:10) | 0 ± 0 | 0 ± 0 |
| Medium 199 + HP (1:500) + antisera (1:100) | 14 ± 10 | 14 ± 0 |
| Medium 199 + HP (1:500) + antisera (1:1000) | 45 ± 7 | 45 ± 7 |

The above experiments indicate that there exists in human blood a single soluble protein which supports epithelial cell spreading and that the latter property is not a function of the totality of serum or plasma but corresponds to a specific protein. This protein supports single cell spreading as well as epithelial sheet movement. It is active at concentrations as low as 1.3 μgm/ml and, although it is active alone, it requires a second non-dialyzable component for maximal activity. The augmenting "co-factor" enhances the spreading activity by about 13×.

A theory as to the mechanism of action of this factor may be formulated from an interpretation of the three assays. In one assay individual cell cytoplasm spreading is measured; in the other two epithelial sheet movement is measured. The significant difference between the latter two assays is the substratum upon which the cell sheets travel. Earlier studies (Stenn, *Brit. J. Derm.*, Vol. 98, pages 411–416 (1978); Stenn et al. (*Biochemistry*, Vol. 11, pages 4502–4515 (1972) had indicated that epithelial cell movement in the outgrowth and epiboly assays occurred, at least for the first three days, even after lethal irradiation. The above experiments indicate that the phenomena in these systems is cell movement, and to a lesser extent, cell division. The aspect of cell movement involved (adhesion, cytoskeleton structuring, metabolism, etc.) and how the effect occurs is, at present, unknown. Because the factor supports maximal spreading in all three systems, it is believed that the same phenomenon occurs in the three assays.

Factors supporting the movement of other types of cells have been described. The epidermal growth factor of Cohen, *J. Biol. Chem.*, Vol. 237, page 1555 (1962), is a small, heat-stable molecule unlike the factor or protein of the invention. Fibronectin has been reported to support the spreading of many different cell types (Ali et al., *Cell*, Vol. 14, pages 439–446 (1978)), but in the mature epithelial systems used here fibronectin is not active. Other workers have studied serum factors which stimulate non-epithelial cell movements in vitro (Burk, *Proc. Nat. Acad. Sci.*, Vol. 70, page 369 (1973); Burk, *Exp. Cell Res.*, Vol. 101, page 293 (1976); and Lipton et al., *Proc. Nat. Acad. Sci.*, Vol. 68, page 2799 (1971)). These studies, however, have been phenomenological so that a molecular comparison is not yet possible.

In view of the fact that the earliest stages of all types of wound repair involve covering the wound by means of active epithelial cell movement such a protein plays an important role in the process of wound closure.

I claim:

1. A trypsin digestible single-chained, glycosylated protein which enhances epithelial cell movement in vivo having the following properties:

(a) a molecular weight of about 62,000 daltons;

(b) resistant to serine protease inhibitors, diisopropyl fluorophosphate and phenyl methyl sulfonyl fluoride;
(c) isoelectric point between 5.1 and 5.2;
(d) extinction coefficient of about 1.0 at 280 nm ultraviolet light, and
(e) an amino acid composition including but not limited to:

| Amino Acid | No. of amino acids per protein molecule 62,752 daltons | No. of amino acid molecules per 1000 amino acids |
|---|---|---|
| Asp | 62 | 111 |
| Thr | 40 | 72 |
| Ser | 46 | 81 |
| Glu | 67 | 119 |
| Pro | 19 | 35 |
| Gly | 26 | 46 |
| Ala | 43 | 77 |
| Val | 33 | 59 |
| Met | 15 | 26 |
| Ile | 24 | 44 |
| Leu | 69 | 123 |
| Tyr | 12 | 22 |
| Phe | 31 | 56 |
| His | 12 | 21 |
| Lys | 34 | 60 |
| Arg | 21 | 37 |
| Trp | 4 | 7 |
| Cys | 2 | 4; |

(f) the N-terminal amino acid is asparagine and the N-terminal amino acid sequence is
$NH_2$-Asparagine-serine-proline-leucine-aspartic-glutamic;
(g) immunoelectrophoresis properties of a serum $\alpha_2$ globulin;
(h) antibody to the protein blocks all the epidermal cell spreading activity of human serum;
(i) antibody to the protein does not react with other known human serum proteins.

2. A method of preparing the protein of claim 1 comprising:
(1) diluting mammalian plasma or serum with water and dissolving therein sufficient ammonium sulfate to produce an approximately 33.3% saturated solution and removing the thus formed precipitate;
(2) dissolving in the solution remaining from step (1) sufficient ammonium sulfate to produce an approximately 66.7% saturated solution;
(3) removing the precipitate from the solution produced by step (2), suspending it in water and dialyzing the suspension against a buffered solution having a pH of about 6.0;
(4) placing the dialyzed fraction in a buffered solution having a pH of about 6.0 and subjecting the solution to anionic chromatographic separation, including washing the chromatographically adhered fraction with said buffered solution;
(5) eluting the chromatographically adhered fraction with a buffered solution having a pH of about 6.0 and an anionic strength of about 12 mmhos;
(6) dialyzing the eluted fraction against a buffered solution having a pH of about 6.0; and
(7) subjecting the dialysand to isoelectric precipitation at a pH of between 4.6 and 5.0 to produce the protein.

3. The method of claim 2 wherein said protein is further purified by gel filtration chromatography and electrophoresis.

4. A method of preparing a factor which enhances the epithelial cell movement activity of the protein of claim 2 comprising;
(1) diluting mammalian plasma or serum with water and dissolving therein sufficient ammonium sulfate to produce an approximately 33.3% saturated solution and removing the thus formed precipitate;
(2) dissolving in the solution remaining from step (1) sufficient ammonium sulfate to produce an approximately 66.7% saturated solution;
(3) removing the precipitate from the solution produced by step (2), suspending it in water and dialyzing the suspension against a buffered solution having a pH of about 6.0;
(4) placing the dialyzed fraction in a buffered solution having a pH of about 6.0 and subjecting the solution to anionic chromatographic separation, collecting the chromatographically non-adhered fraction with said buffered solution.

5. The product of claim 4.

* * * * *

UNITED STATES PATENT AND TRADEMARK OFFICE
CERTIFICATE OF CORRECTION

PATENT NO. : 4,431,582
DATED : February 14, 1984
INVENTOR(S) : Kurt S. Stenn

It is certified that error appears in the above-identified patent and that said Letters Patent are hereby corrected as shown below:

Column 2, line 61 "62" should read as --40--.

Signed and Sealed this

Fourth Day of December 1984

[SEAL]

Attest:

GERALD J. MOSSINGHOFF

Attesting Officer

Commissioner of Patents and Trademarks